US006448549B1

(12) United States Patent
Safaee-Rad

(10) Patent No.: US 6,448,549 B1
(45) Date of Patent: *Sep. 10, 2002

(54) BOTTLE THREAD INSPECTION SYSTEM AND METHOD OF OPERATING THE SAME

(75) Inventor: Reza Safaee-Rad, Mississauga (CA)

(73) Assignee: Image Processing Systems, Inc., Ontario (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/011,510
(22) PCT Filed: Aug. 2, 1996
(86) PCT No.: PCT/CA96/00527
§ 371 (c)(1), (2), (4) Date: Feb. 2, 1998
(87) PCT Pub. No.: WO97/06429
PCT Pub. Date: Feb. 20, 1997

Related U.S. Application Data

(63) Continuation-in-part of application No. 08/511,249, filed on Aug. 4, 1995, now abandoned.

(51) Int. Cl.$^7$ .................................................. G01N 9/04
(52) U.S. Cl. .............................. 250/223 B; 356/239.4
(58) Field of Search .................... 250/223 B, 223 R, 250/557.42, 559.49; 382/142; 356/239.4, 239.5; 348/127; 209/524, 526

(56) References Cited

U.S. PATENT DOCUMENTS 2,798,605 A 7/1957 Richards .................... 209/524
3,932,042 A 1/1976 Faani et al. ............... 356/239.4
4,293,219 A * 10/1981 Ducloux ................... 356/239.4

(List continued on next page.)

FOREIGN PATENT DOCUMENTS

EP 0 209 077 1/1987

OTHER PUBLICATIONS

*IEEE Transactions on Pattern Analysis and Machine Intelligence*, vol. 3, No. 5, Sep. 1981, New York, A. Rosenfeld et al. "Threshold Using Relaxation", pp. 598–606, XP000605134.

Patent Abstracts of Japan, vol. 9, No. 90, (P-350) [1813], Apr. 19, 1985 & JP,A,59 217141 (Mitsubishi Denki K.K.) Dec. 7, 1987.

Primary Examiner—Seungsook Ham
Assistant Examiner—Thanh X. Luu
(74) Attorney, Agent, or Firm—Connolly Bove Lodge & Hutz LLP

(57) ABSTRACT

A method of inspecting a bottle (14) having a threaded section (104) for thread defects as the bottle moves along a production line (10) requires video images (100) of the bottle to be taken as the bottle moves into the fields of view of video cameras (22). Each video image encompasses a general region of interest (108) which contains at least a portion of the threaded section of the bottle. The position of the bottle (14) within the video image is then determined based on the location of the top rim (110) of the bottle within the video image. A portion of the general region of interest which encompasses at least a portion of the threaded section of the bottle is segmented into a plurality of specific regions of interest (120, 122). Pixels of the video image within the specific regions of interest are then examined to detect thread defects.

33 Claims, 10 Drawing Sheets

U.S. PATENT DOCUMENTS

| | | | |
|---|---|---|---|
| 4,553,838 A | 11/1985 | Madsen | 356/237.1 |
| 4,606,635 A | 8/1986 | Miyazawa et al. | 356/240.1 |
| 4,691,231 A | 9/1987 | Fitzmorris et al. | 348/127 |
| 4,701,612 A | 10/1987 | Sturgill | 250/223 B |
| 4,731,649 A | 3/1988 | Chang et al. | 348/127 |
| 4,758,084 A | 7/1988 | Tokumi et al. | 356/239.4 |
| 4,831,250 A | 5/1989 | Fukuchi et al. | 250/223 B |
| 5,007,096 A | 4/1991 | Yoshida | 382/142 |
| 5,136,157 A | 8/1992 | Apter et al. | 250/223 B |
| 5,262,871 A | 11/1993 | Wilder et al. | 348/307 |
| 5,369,713 A | 11/1994 | Schwartz et al. | 382/142 |
| 5,453,612 A | 9/1995 | Toyama et al. | 250/223 B |

\* cited by examiner

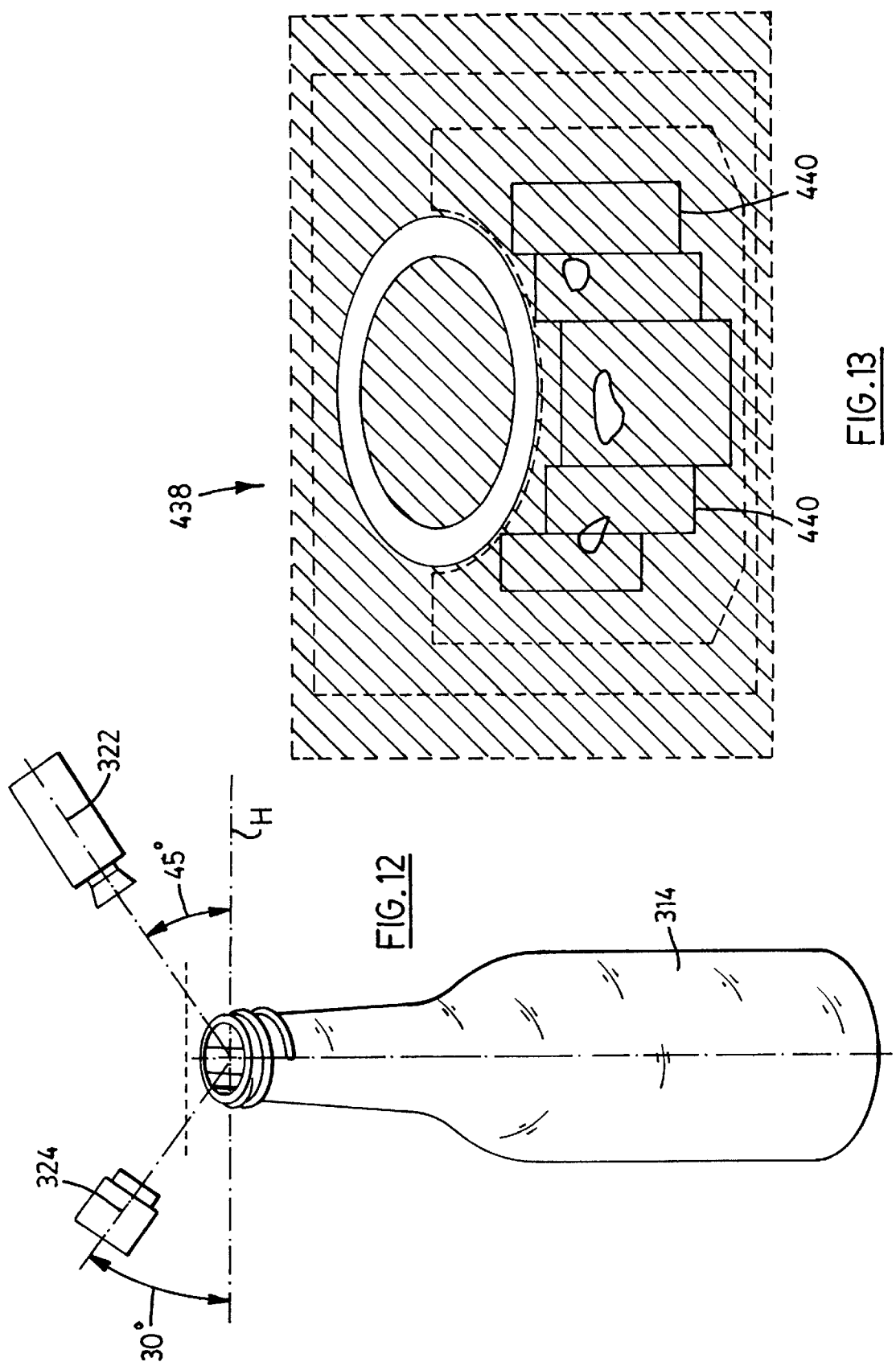

BOTTLE THREAD INSPECTION SYSTEM AND METHOD OF OPERATING THE SAME

This application is a 371 of PCT application Ser. No. CA96/00527 filed Aug. 02, 1996 and a continuation-in-part of U.S. application Ser. No. 08/511,249, filed Aug. 04, 1995 now abandoned.

FIELD OF THE INVENTION

The present invention relates to bottle inspection systems and in particular to an inspection system and method for detecting thread defects in bottles.

BACKGROUND OF THE INVENTION

Conventional bottle processing equipment moves bottles at high speed along a production line. It is important to inspect the bottles to detect bottles having defects. These defects include, but are not limited to, cracks or chips within the thread area around the neck of the bottle. When necessary, bottles with defects are rejected, i.e., removed from the production line. Because of the speed at which the production lines operate, very fist defect detection is required. Computerized video image analysis well suited for this purpose due to its non-contact nature, high speed, decision-making capability, and ability to analyze a large bottle area with each video image.

Inspection systems to detect thread defects in bottles moving along a production line have been developed. For example, U.S. Pat. No. 3,848,742 to Krenmayr discloses a system for detecting various types of defects inside the glass at the bottle neck. During operation of this system, the bottle is rotated in-place 360 degrees about its central vertical axis and must be accurately positioned in the inspection area. These requirements slow the inspection speed of the system allowing the system to inspect only a small number of bottles per minute (for example, 200 90-gram bottles per minute).

U.S. Pat. No. 4,701,612 to Strugil and U.S. Pat. No. 4,958,223 to Juvinall, both of which have the same assignee, disclose inspection Systems which require glass or plastic containers to be held in vertical orientations and rotated 360 degrees about their central axes. Furthermore, the systems require gray-level pattern matching, that is, the gray-level image of the area of the bottle under inspection must be compared with a standard image indicative of an acceptable container. To implement pattern matching of this nature, pre-processing is required to achieve standard orientation before the pattern matching process can be carried out. All these requirements result in an overall low inspection rate deficiency.

U.S. Pat. No. 5,126,556 to Domenico et al. discloses three methods for inspecting bottles to detect thread defects. The first two methods are based on precise positioning of a bottle in the inspection area. Specifically, the central vertical axis of a bottle must coincide with the optical axis of the imaging system. The third method, however, requires a bottle to be rotated 90 degrees about its central vertical axis while the bottle is moving along a conveyor. In all three methods, defect detection is based on gray-level pattern matching. As mentioned above, initial preprocessing is required before pattern matching can be implemented.

U.S. Pat. No. 5,444,535 to Axelrod discloses a high signal-to-noise optical apparatus and method for glass bottle thread damage detection. The apparatus includes a source for directing light against a s target surface. The source is selected to emit light at wavelengths substantially overlapping a target glass absorption bandwidth A first optical polarizer polarizes light emitted from the light source prior to the light impinging on the target glass surface . A light detector in the form of a photodetector and a second optical polarizer arranged in cross-polarized relation to the first optical polarizer are aligned in a scattered light beam detecting relation relative to the incident beam on the glass target surface. The light detector is at an angle in the Brewster range and generates a detected signal in response to light scattered through defects in the target glass surface.

Although the above references disclose inspection systems for detecting thread defects in bottles, improved systems to detect thread defects in bottles more quickly and accurately are continually being sought.

It is therefore an object of the present invention to provide a novel method and system for inspecting bottles to detect thread defects.

SUMMARY OF THE INVENTION

According to one aspect of the present invention there is provided a method of inspecting a bottle having a threaded section for thread defects as said bottle moves along a production line comprising the steps of:

(i) capturing a video image of said bottle with a video camera as said bottle moves into the field of view of said video camera without requiring said bottle to be at a specific position within said field of view, said video image encompassing a general region of interest containing at least a portion of the threaded section of said bottle;

(ii) determining the position of said bottle within said general region of interest based on the location of a feature of said bottle within said general region of interest;

(iii) segmenting a portion of said general region of interest which encompasses said at least a portion of said threaded section into a plurality of specific regions of interest; and (iv) examining pixels of said video image in said specific regions of interest to detect thread defects.

In the preferred embodiment, the feature of the bottle determined at step (ii) is the top rim of the bottle. Once the top rim of the bottle is established, a reference location based on the position of the bottle is then determined. The portion of the general region of interest and the positions of the specific regions of interest are then determined based on the position of the reference location.

In one embodiment, the reference location is positioned at the center of the top rim and a central specific region of interest is determined relative to the reference location. The positions of the other specific regions of interest on opposite sides of the central specific region of interest are then determined relative to the position of the central specific region of interest. Preferably, the other specific regions of interest are increasingly offset in a Y-direction the further they are from the central specific region of interest to follow the threaded section of the bottle in the video image. It is also preferred that the other specific regions of interest decrease in width (i.e. in an X-direction) the further they are from the central specific region of interest to compensate for perspective effects.

In a preferred embodiment, during step (iv), a black/white pixel threshold value is determined for the specific regions of interest. The pixels of the video image within the specific regions of interest are compared with the pixel threshold value and the pixels are binarized as white or black depending on the results of the comparisons. Groups of contiguous white pixels larger than a threshold number are filtered and if the shapes of the groups of contiguous white pixels do not resemble bottle threads, the groups of contiguous white pixels are determined to be thread defects.

According to another aspect of the present invention there is provided a system for inspecting bottles having a threaded section as said bottles are moved along a production line comprising:

a plurality of video imaging sections disposed along said production line at spaced locations, each video imaging section being oriented with respect to said production line to take a video image of each bottle at a different circumferential region thereof as each bottle moves into the field of view of said video imaging section without requiring said bottle to be at a specific location in said field of view, said video images encompassing a general region of interest containing at least a portion of the threaded section of each bottle; and processing means in communication with said video imaging sections and receiving the video images taken thereby, said processing means processing each video image to determine the position of said bottle within said general region of interest based on the location of a feature of said bottle within said general region of interest; segmenting a portion of said general region of interest which encompasses said at least a portion of said threaded section into a plurality of specific regions of interest; and examining pixels in said specific regions of interest to detect thread defects.

In a preferred embodiment, each video imaging section includes a video camera and a light source. The light source and the video camera are positioned on opposite sides of the production line and are oriented so that video images of the entire circumference of each bottle are taken. in one embodiment the processing means signs a bottle reject mechanism downstream of the inspection system when a defective bottle is detected so that the defective bottle can be removed from the production line.

According to yet another aspect of the present invention there is provided a system for inspecting bottles having a threaded section as said bottles are moved along a production line comprising:

a plurality of video imaging sections disposed along said production line at spaced locations, each video imaging section being oriented with respect to said production fine to take a video image of each bottle at a different circumferential region thereof as each bottle moves into the field of view of said video imaging section without requiring said bottles to be at a specific location in said field of view, said video imaging sections being arranged to reduce spacing therebetween; and processing means in communication with said video imaging sections and receiving the video images taken thereby, said processing means processing said video images to detect thread defects in said bottle.

In a preferred embodiment, each video imaging section includes a video camera and a light source. The light source and the video camera are positioned on opposite sides of the production line and are laterally offset so that the optical axes of the video imaging sections form oblique angles with respect to the direction of travel of the bottles. It is also preferred that the video imaging sections are arranged in an upstream pair and a downstream par with the optical axes of the upstream pair forming obtuse angles with respect to the direction of travel of the bottles and with the optical axes of the downstream pair forming acute angles with respect to the direction of travel of the bottles.

According to yet another aspect of the present invention there is provided a method of locating the position of a bottle within a video image comprising the steps of:

capturing a video image of at least a portion of said bottle with a video camera;

digitizing said video image;

comparing pixels in said video image with a threshold value and binarizng said pixels as white or black depending on the results of said comparisons; and determining the position of said bottle relative to the boundaries of said video image based on the location of the largest group of contiguous white pixels within said video image.

In still yet another aspect of the present invention there is provided method of detecting defects in bottle threads comprising the steps of:

capturing a video image of said bottle threads;

segmenting at least a portion of said video image into a plurality of specific regions of interest; and video processing each specific region of interest independently to determine defects in each of said specific regions of interest based on the existence of white areas larger than a prescribed threshold area size within said specific regions of interest.

According to still yet another aspect of the present invention there is provided a system for locating the position of a bottle within a video image comprising:

means for back lighting said bottle with a light source;

a video camera for capturing a video image of at least a portion of said bottle within the field of view thereof;

means for digitizing said video image; and means for determining the position of said bottle within said video image based on the location of the largest white area within said video image.

According to still yet another aspect of the present invention there is provided a system for detecting defects in bottle threads comprising:

means for capturing a video image of said bottle threads;

means for segmenting at least a portion of said video image into a plurality of specific regions of interest; and means for video processing each specific region of interest independently to determine defects in each of said specific regions of interest based on the existence of white areas larger than a prescribed threshold area size within said specific region of interest.

The present invention provides advantages in that thread defects in bottles can be detected without requiring handling of the bottles and while the bottles are moving at a high rate of speed along the production line. When a defective bottle is detected, the inspection system signals a bottle reject mechanism to allow the defective bottle to be removed from the production line without slowing movement of the bottles along the production line.

BRIEF DESCRIPTION OF THE DRAWINGS

Embodiments of the present invention will now be described more fully with reference to the accompanying drawings in which:

FIG. 12 is a perspective view showing a portion of the inspection system illustrated in FIG. 11; and FIG. 13 is an illustration of a binarized video image taken by the inspection system of FIG. 10 showing specific regions of interest and thread defects therein.

DESCRIPTION OF THE PREFERRED EMBODIMENTS

Figure 1:
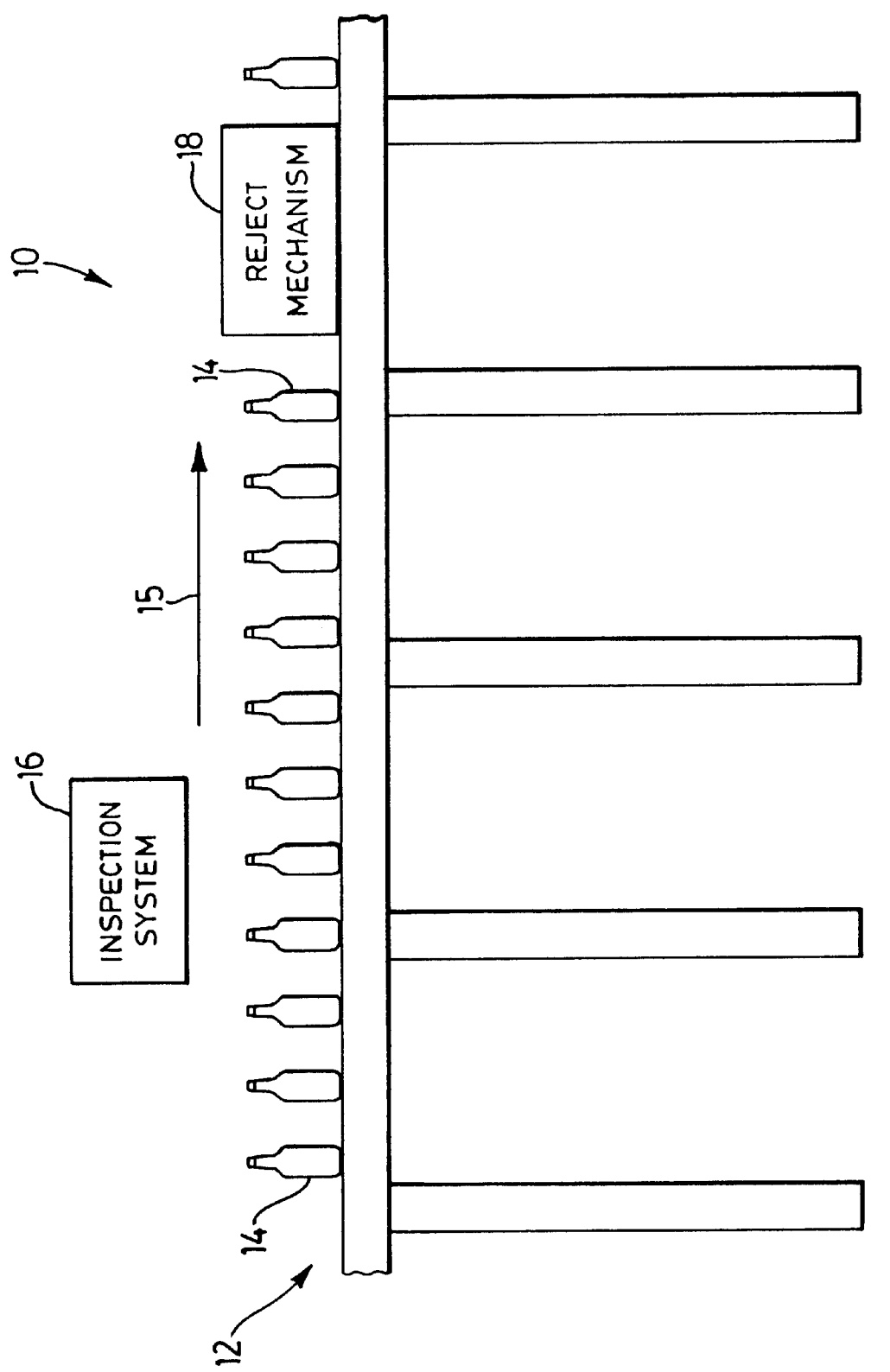
FIG. 1 is a schematic side elevational view of a portion of a bottle production line including an inspection system for detecting bottle defects in accordance with the present invention.

Referring now to FIG. 1, a portion of a line in a bottling facility is shown and is generally indicated to by reference numeral 10. The production line includes a conveyor system 12 to move glass bottles 14 along a path indicated by reference numeral 15 at a high rate of speed typically in the range of 800 to 1350 bottles per minute between various stations located along the production line. Positioned along the production line is an inspection system 16 to inspect the threaded section of each glass bottle 14 for defects as the bottles move along the conveyor system 12 without require the bottles 14 to be handled. Downstream of the inspection system 16 is a bottle reject mechanism 18. Bottle reject mechanism 18 is responsive to the inspection system 16 and removes defective bottles from the production line so that these bottles do not travel downstream to the other stations in the bottling facility.

Figure 2:
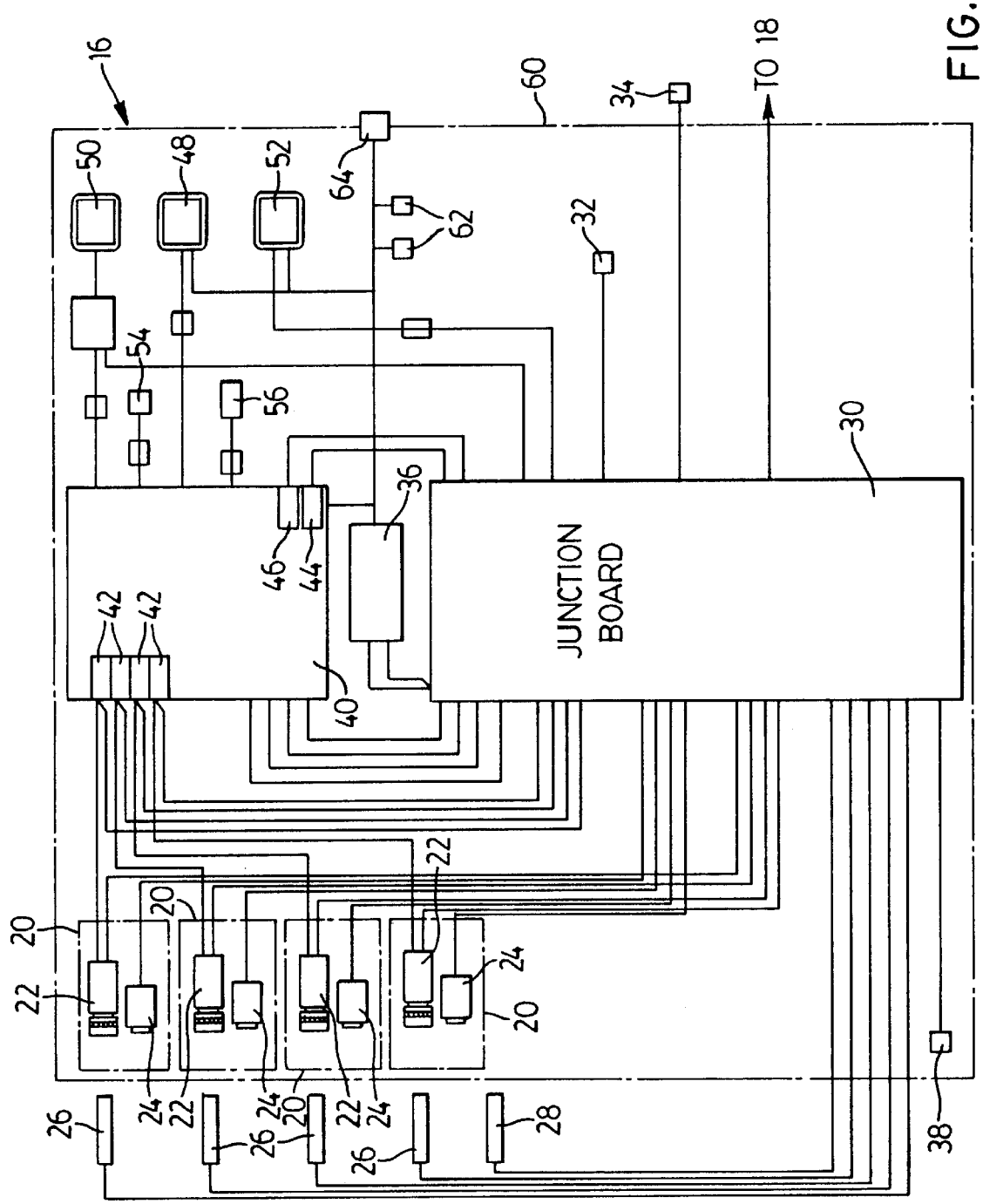
FIG. 2 is a schematic block diagram of the inspection system illustrated in FIG. 1.

Referring now to FIG. 2, the inspection system 16 is better illustrated. As can be seen, the inspection system includes a plurality of video imaging sections 20 positioned above the conveyor system 12 at spaced locations. Each video imaging section 20 includes a Pulnix CCD) camera 22 and a halogen lamp 24. A bottle detection sensor 26 is associated with each video imaging section 20. The bottle detection sensors are positioned along the conveyor system 12 adjacent their associated video imaging section 20. An additional bottle detection sensor 28 is positioned along the conveyor system 12 downstream of the video imaging sections 20 to detect bottles as they exit the inspection system 16. The bottle detection sensors 26 and 28 are preferably photoelectric such as those manufactured by Omron.

The bottle detection sensors 26 and 28, CCD cameras 22 and halogen lamps 24 are connected to a junction board 30. A temperature sensor 32, an encoder 34 and a lamp power supply 36 are also connected to the junction board 30. Encoder 34 is located along the conveyor system 12 and detects the speed of the bottles 14 as they move along the conveyor system 12. The junction board 30 is also connected to an alarm 38 in the form of a beacon and to the bottle reject mechanism 18. Also connected to the junction board 30 is a computer 40.

Computer 40 includes a plurality of video image processors 42, each video image processor of which is associated with one of the CCD cameras 22. Each video image processor 42 includes an ARTVC daughterboard to capture video images output by the CCD cameras 22 and a motherboard to process and analyze the video images captured by the daughterboard to detect bottle thread defects as will be described. The video image processors 42 capture and process video images output by the CCD cameras 22 in response to the bottle detection sensors 26. A production line board 44 wit the computer 40 is also responsive to the bottle detection sensors 26 and 28 and to the encoder 34 and keeps track of the positions of bottles as they move through the inspection system 16 to allow detected defective bottles to be tracked and removed from the conveyor system 12 by the bottle resect mechanism 18. A PCOM board 46 within the computer 40 monitors and tests the inspection system 16 to detect alarm conditions as will be described.

An operator monitor 48 and an associated touch screen 50 are also connected to the computer 40 to allow an operator to input commands to the inspection system 16 and to view the results of the bottle inspections. A live monitor 52 is also connected to the computer 40 by way of the junction board 30 and displays a video image of the last defective bottle to pass a video imaging section 20. Input devices such as a mouse 54 and keyboard 56 are also connected to the computer 40 to allow the inspection system to be initialize and reprogrammed if required The components of the inspection system 16 with the exception of the bottle detection sensors 26 and 28 are accommodated in a cabinet ( not shown) which straddles the conveyor system 12. Fans 62 are mounted in the cabinet to moderate the temperature therein. A switchable power supply module 64 is connected to AC mains and supplies power to the fans 62, the lamp power supply 54, the live and operator monitors 52 and 48 respectively and the computer 40.

Figure 3:
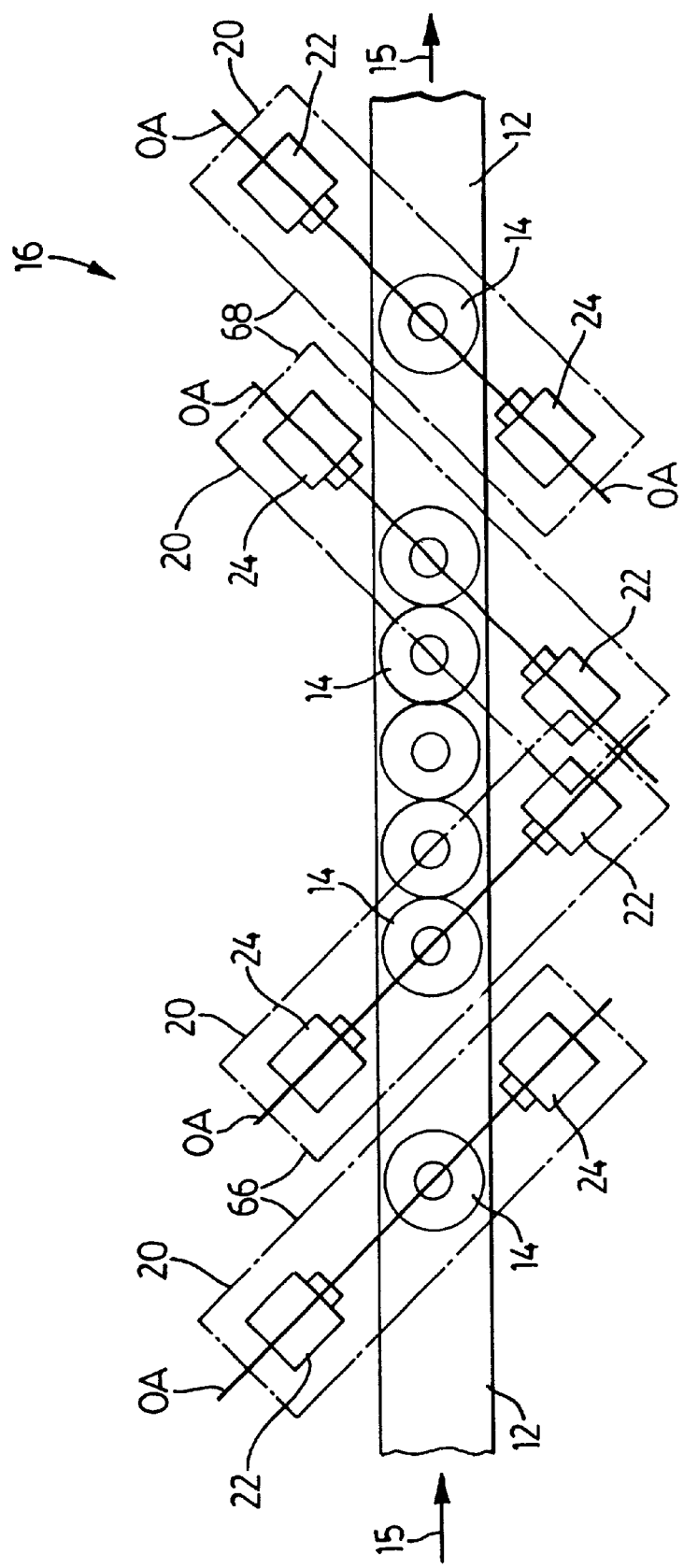
FIG. 3 is a top plan view of a portion of the inspection system illustrated in FIG. 1.

Referring now to FIG. 3, the video imaging sections 20 are better illustrated. As can be seen, the CCD camera 22 and halogen lamp 24 of each video imaging section are positioned on opposite sides of the conveyor system 12. The CCD cameras and halogen lamps are also arranged in interlocking, upstream and downstream shielded pairs 66 and 68 respectively to reduce the length of the inspection system 16 along the conveyor system 12 and to reduce interference between adjacent video imaging sections 20. Specifically, the CCD camera 22 and halogen lamp 24 in each of the video imaging sections 20 are positioned on opposite sides of the conveyor system 12 and are laterally offset so that the optical axis OA of each video imaging section forms an oblique angle with respect to the path 15 of the bottles as they travel along the conveyor system 12. In particular, the optical axes of the upstream pair 66 of video imaging sections 20 form obtuse angles with respect to the path 15 while the optical axes of the downstream pair 68 of video imaging sections 20 form acute angles with respect to the path 15. The positions of the CCD cameras 22 and halogen lamps 24 with respect to the sides of the conveyor system 12 alternate in successive video imaging sections 20.

The field of view of each CCD camera 22 includes approximately 110 degrees of the circumference of the threaded section of a bottle 14. The alternating positions of the CCD cameras 22 and halogen lamps 24 in successive video imaging sections 20 and the orientation of the CCD cameras and halogen lamps in the video imaging sections 20 ensure that the fields of view of the CCD cameras 22 overlap and encompass the entire circumference of a bottle 14 as it travels through the iron system 16. The reduced spacing between successive video imaging sections 20 and the overlapping fields of view of the CCD cameras 22 minimize the likelihood of a bottle rotating on the conveyor system 12 about its central longitudinal axis as it travels between the successive video image sections by an amount which results in a region of the threaded section of the bottle not being captured in a video image taken by any of the video imaging sections 20. In this manner, multiple video images of the bottle can be taken a synchronously by the video imaging sections 20 while ensuring that the video images encompass the entire circumference of the threaded section of the bottle.

Figure 4:
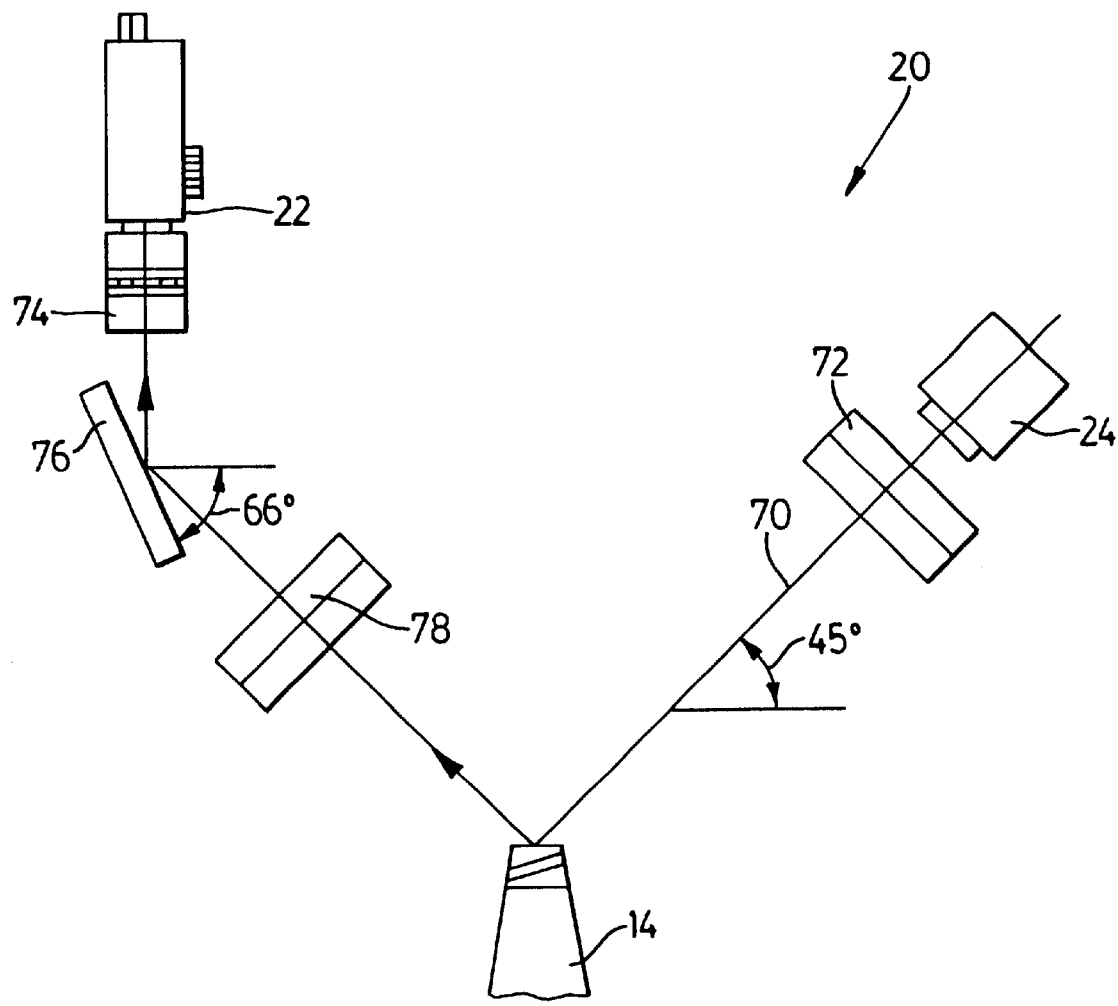
FIG. 4 is a side elevational view of a portion of the inspection system illustrated in FIG. 1.

FIG. 4 best illustrates the orientation of the CCD camera 22 and halogen lamp 24 in one of the video imaging sections 20. Those of skill in the art will appreciate that the orientation of the CCD cameras 22 and halogen lamps 24 is the same in each of the video imaging sections. As can be seen, the halogen lamp 24 is suspended from the cabinet and oriented to direct light 70 downwardly towards a bottle 14 at about a 45 degree angle to backlight the bottle. A double pane window 72 is positioned in front of the halogen lamp 24 and is oriented so that the beam of light 70 is generally normal to the plane of the pane window 72. One of the panes of the window 72 is slidable relative to the other of the panes to allow the window 72 to be cleaned.

The CCD camera 22 is suspended from the cabinet and is oriented with its lens 74 pointing down in a direction parallel to the longitudinal axis of the bottle 14. An angled mirror 76, positioned below the CCD camera 22, is also suspended from the cabinet and directs light reflected from the bottle 14 towards the CCD camera 22. The mirror is angled such that it forms about a 65 degree angle with respect to the plane of the lens 74 of the CCD camera 22. A double pane window 78 is positioned between the mirror 76 and the bottle 14 and is oriented so that its plane is normal to light reflected from the bottle and directed towards the mirror 76. One of the panes of the window 78 is slidable relative to the other of the panes to allow the window 78 to be cleaned. The windows 72 and 78 may be coated with an anti reflection coating if desired. The angled direction of the fight 70 generated by the halogen lamp 24 and the orientation of the mirror 76 and windows 72 and 78 have been found to allow thread defects to be consistently detected while reducing total internal reflection.

Although not illustrated, the windows 72 and 78 are mounted on an inverted zigzag-shaped support that extends across the cabinet. This allows the support to accommodate the windows 72 and 78 of each video imaging section 20 at spaced locations along its length.

Figure 5:
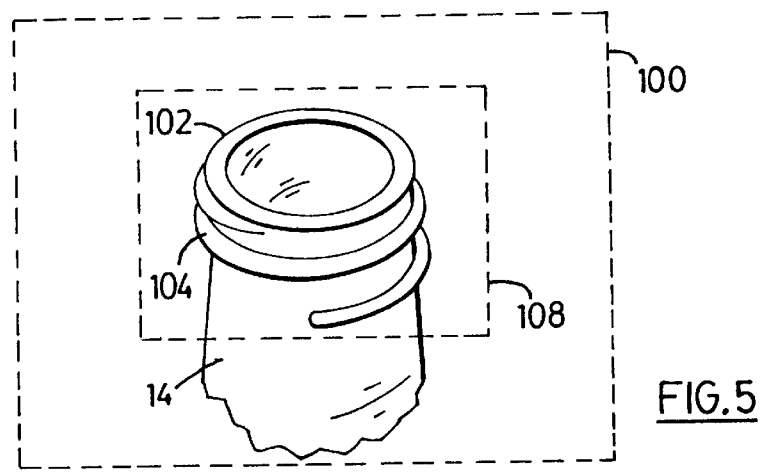
FIG. 5 is an illustration of a video image of a bottle taken by the inspection system of FIG. 1.

During operation, when a bottle 14 moves along the conveyor system 12 and passes a bottle detection sensor 26, the bottle detection sensor 26 detects the presence of the bottle 14 and outputs a bottle detection signal. Bottle detection signal is received by the junction board 30 and is passed to the associated CCD camera 22 as well as to the computer 40. The CCD camera 22 responds to the bottle detection signal by opening its shutter so that a video image 100 of the rim 102 and threads 104 of the bottle 14 is taken, as shown in FIG. 5. The computer 40 uses the bottle detection signal to activate the video image processor 42 associated with the CCD camera 22 so that the video image taken by the CCD camera 22 is captured by the daughterboard therein. The computer 40 also conveys the bottle detection signal to the production line board 44 so that the bottle 14 can be counted and its position as it travels through the inspection system 16 tracked. The video image 100 captured by the daughterboard in the video image processor 42 is then analyzed by the CPU in the motherboard of the video image processor 42 to detect thread defects as will be described. Since the inspection system 16 includes four bottle detection sensors 26 and associated CCD cameras 22 and video image processors 42, the above process is performed four times as each bottle travels through the inspection system 16.

If no significant defects are found in the threads 104 of the bottle 14 as the video images 100 are analyzed, the bottle is allowed to continue along the conveyor system 12. However, if a significant defect in the threads 104 of the bottle 14 is detected, the production line board 44 signals the bottle reject mechanism 18 via the junction board 30 to allow the bottle react mechanism to remove the defective bottle from the conveyor system 12 when the defective bottle reaches the bottle reject mechanism.

Specifics of the manner in which the captured video images are analyzed by the CPUs in the video image processor motherboard to detect bottle thread defects will now be described.

When a video image 100 is captured by a video image processor 42, the video image is digitized and is stored in memory as a two dimensional matrix of pixels, typically 512×480 pixels, covering a field of view of about 50 mm ×50 mm, so that each pixel represents about 0.1 mm ×0.1 mm of the video image. Following this, the CPU in the motherboard collects a histogram on the pixels in a rectangular window 108 within the video image 100. The rectangular window 108 may include between 75% to 100% oft he pixels within the video image 100. A black/white hold value is then calculated for the video image 100 using the Oust Method, as described in an article entitled "A Threshold Selection Method From Gray-level Histogram" by H. Otsu, in IEEE Transactions on Systems, Man and Cybernetics, Vol. SMC-9, pp. 62–69, 1979, the content of which is incorporated herein by reference. The calculated threshold value is then offset by an empirically determined amount. The actual threshold value used is based on a running average of the offset Otsu threshold values calculated above for the video images captured by the video image capture board 42. This allows the inspection system 16 to compensate for aging, dirt accumulation etc. which typically results in darker video images.

The pixels in each scan line within the window 108 are then run length coded. In particular, initially the pixels in each scan line are assumed to have a grey-level value below the actual threshold value. Adjacent pixels in each scan line are then compared. During each comparison, the addresses of the pixels which change from below the actual threshold value to above the actual threshold value and which change from above the actual threshold value to below the actual threshold value are recorded. Pixels which change from below the actual threshold value to above the actual threshold value are designated as white, while pixels which change from above the actual threshold value to below the actual threshold value are designated as black. Thus, pairs of pixel addresses are stored for each scan line with the first address of each pair representing the beginning of a segment of white pixels and the second address of each pair representing the end of the segment of white pixels.

Figure 6:
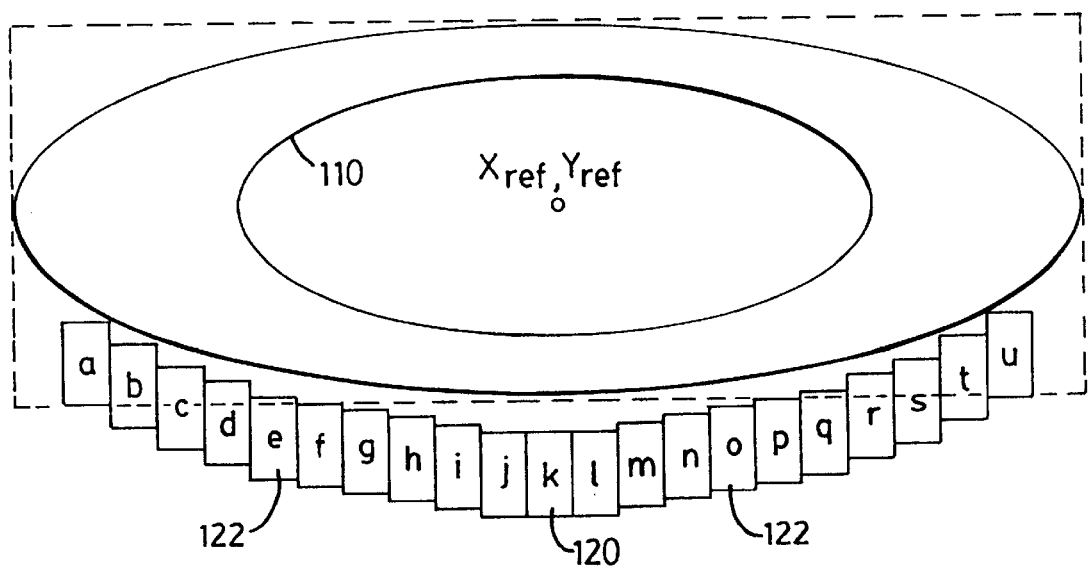
FIG. 6 is an illustration of a binarized video image and showing specific regions of interest within the video image.

Following the above, the CPU examines the run length coded data to locate a reference feature of the captured video image. In the present embodiment the reference feature is the top rim 102 oft he bottle 104 and appears a torus of contiguous white pixels. Specifically, the CPU performs blob detection on the run length coded data to locate the segments of white pixels which resemble the torus. FIG. 6 is a negative oft he pixels in the window 108 forming the torus (generally indicated to by reference numeral 110).

Once the torus 110 of white pixels is located, an enclosing rectangle 112 aligned with the scan lines which encompasses the torus 110 is defined. The center of the rectangle 112 is calculated and is used as a reference location Xref Yref. After the reference location Xref, Yref is established, a rectangular, central specific region of interest 120 within the window 108 which encompasses a portion of the threads 104 of the bottle 14 is determined by moving downwardly from the reference location in the Y-direction by a predetermined number of pixels. Once, the central specific region of interest 120 is determined, ten other rectangular specific regions of interest 122 on both sides of central specific region of interest 120 are also determined giving a total of 21 specific regions of interest. The specific regions of interest 122 are increasingly offset in the Y-direction the further they are away from the central specific region of interest 120 so that they follow the threads of the bottle about its circumference. The dimensions of the specific regions of interest 122 also decrease in the X-direction the further they are from the central specific region of interest 120 to compensate for the perspective effects. Thus, the numbers of pixels within the specific regions of interest 120 and 122 vary, although each specific region of interest has approximately 1000 pixels (50×20 pixels).

Following the above, the CPU calculates a black/white threshold value for each of the specific regions of interest 120 and 122. The black/white threshold value calculated for each of the specific regions of interest is based on the actual threshold value determined previously. However, the actual threshold value is scaled for each specific region of interest by subtract an empirical offset. The empirical offset increases for specific regions of interest 122 further from the central specific region of interest 120. Thus, the black/white threshold values decrease in magnitude the further the specific region of interest is from the central specific region of interest. With the threshold values established for the specific regions of interest, the CPU compares the pixels in the specific regions of interest within the window 108 with the threshold value and designates the pixels as white or black depending on the results of the comparisons to generate binarized pixels. Blob detection is then performed on the binarized pixels in each of the specific regions of interest to locate groups of contiguous white pixels in each specific region of interest.

Figure 7A:
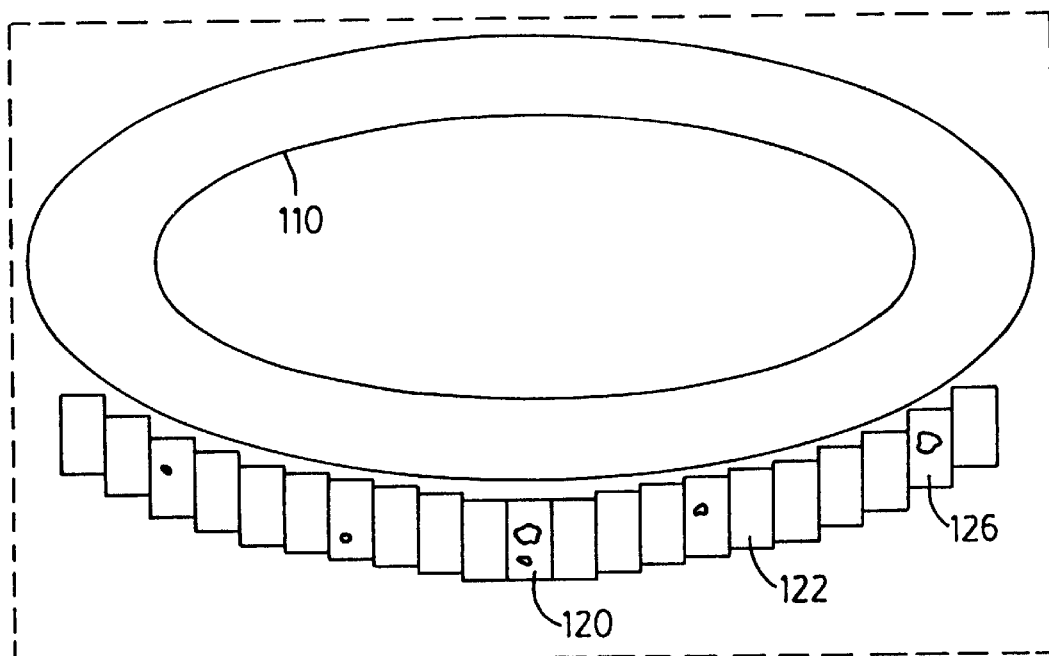
FIG. 7a is an illusion of the specific regions of interest within the video image after being binarized to show thread defects.
Figure 7B:
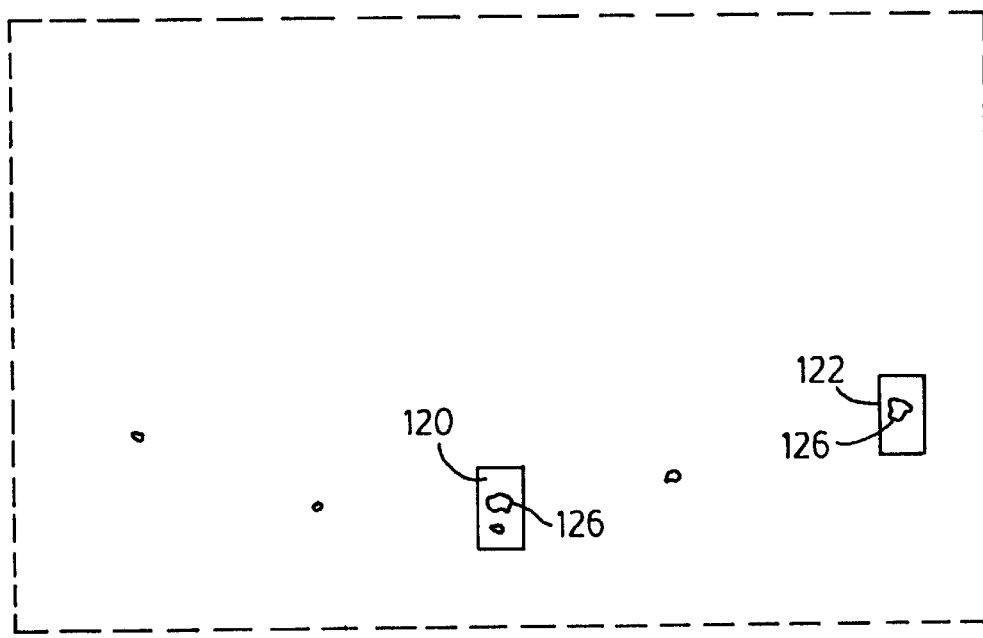
FIG. 7b is an illustration of specific regions of interest containing significant thread defects.

The CPU then collects a histogram for each specific region of interest by counting the number of pixels in the various groups. The areas of the groups of contiguous pixels detected in the specific regions of interest 122 are then scaled according to their positions relative to the central specific region of interest 120 to correct for perspective effects which make a given defect appear smaller in the outer specific regions of interest 122 than it would appear in the central specific region of interest 120. Groups of pixels having five or fewer contiguous binarized pixels are discarded. The binarized pixels of the remaining groups are then Summed and the sum is compared with a threshold area value. If the sum exceeds the threshold area value, the groups of contiguous white pixels are filtered to reduce false detection of thread defects. In particular, the shape and area characteristics of the contiguous white pixels are examined to determine if they resemble the threads of a bottle. If a match is determined, the CPU determines that the generated white pixels are not a result of a thread defect but rather a result of a well defined thread. However, if a match is not determined, a defect 126 is considered to be located in the threads of the bottle (see FIGS. 7a and 7b).

During the above process, the torus 110 and the outlines oft he specific areas of interest are displayed on the operator monitor 48 superimposed on the video image. Groups of contiguous white pixels are also displayed on the operator monitor 48 within the appropriate outline of the specific area of interest.

Once a thread defect is detected, the CPU outputs the captured image to the live monitor 52 via the junction board 30 so that the defective bottle is displayed. The CPU also signals the production line board 44 so that the defective bottle can be tracked. When the defective bottle reaches the bottle detection sensor 28 and is detected, the production line board 44 signals the bottle reject mechanism 18 via the junction board 30 so that the bottle reject mechanism can track the defective bottle and remove it from the conveyor system 12 when the defective bottle reaches the bottle reject mechanism.

The above described process is performed for the video images captured by each of the video image processors 42. Thus, as each bottle 14 travels along the inspection system 16, four video images of the rim and threads of the bottle are taken. Since these video images encompass approximately 110 degrees of the bottle circumference and are taken about the circumference of the bottle at approximately 90 degree spacings, the entire threaded section of each bottle is examined for defects.

In addition to the above, the PCOM board 46 in the computer 40 monitors the output oft he temperature sensor 32 by way of the junction board 30. If the detected temperature exceeds a threshold value, the PCOM board 40 activates the beacon 38 via the junction board 30. The PCOM board 46 also monitors the junction board 30 to determine if the halogen lamps 24 are drawing current. If any one of the halogen lamps 24 is determined not to be drawing cure the PCOM board 46 activates the beacon 38 via the junction board 30. Since the inspection system 16 typically operates unattended, the activation of the beacon 38 allows fault conditions in the operation of the inspection system 16 to be detected by an operator.

Although a particular example of blob detection has been described to detect contiguous white pixels, those of skill in the art will appreciate that other methods can be employed such as the method as described in an article by G. Hirzinger and K. Landzattel entitled "A Fast Technique for Segmentation and Recognition of Binary Patterns", IEEE Conference on Pattern Recognition and Image Processing, 1981, Run-Length Connectivity Analysis as described in an article by I. Kabir, entitled "A Computer Vision System Using Fast One Pass Algorithms", M. S. Thesis, University of California, Davis, 1983, the Clustering Method as described in an article by R. C. Smith and A Rosenfeld, entitled "Threshold Using Relaxation", IEEE Trans. on Pattern Analysis and Machine Intelligence, Vol. 3, pp. 598–605, 1981, the Region Growing Method as described in an article by C. R. Brice and C. L. Fenneman, entitled "Scene A is Using Regions", Artificial Intelligence, Vol. 1, pp. 205–226, 1970, and the Split and Merge Method as described in an article by D. M. Mark and D. J. Abel entitled "Linear Quadtrees from Vector Representation of Polygons", IEEE Trans. on Pattern Analysis and Machine Intelligence, Vol. PAMI-7, No. 3, pp. 344–349, 1985.

As shown, the present invention provides a computerized video analysis method of detecting thread defects in glass bottles without requiring the bottles to be handled or requiring the conveyor system 12 to slow down. Moreover, by using computerized video analysis, the bottles need not be positioned precise prior to analysis. Since the bottles do not need to be handled, damage to and contamination of the bottles is reduced.

Figure 8:
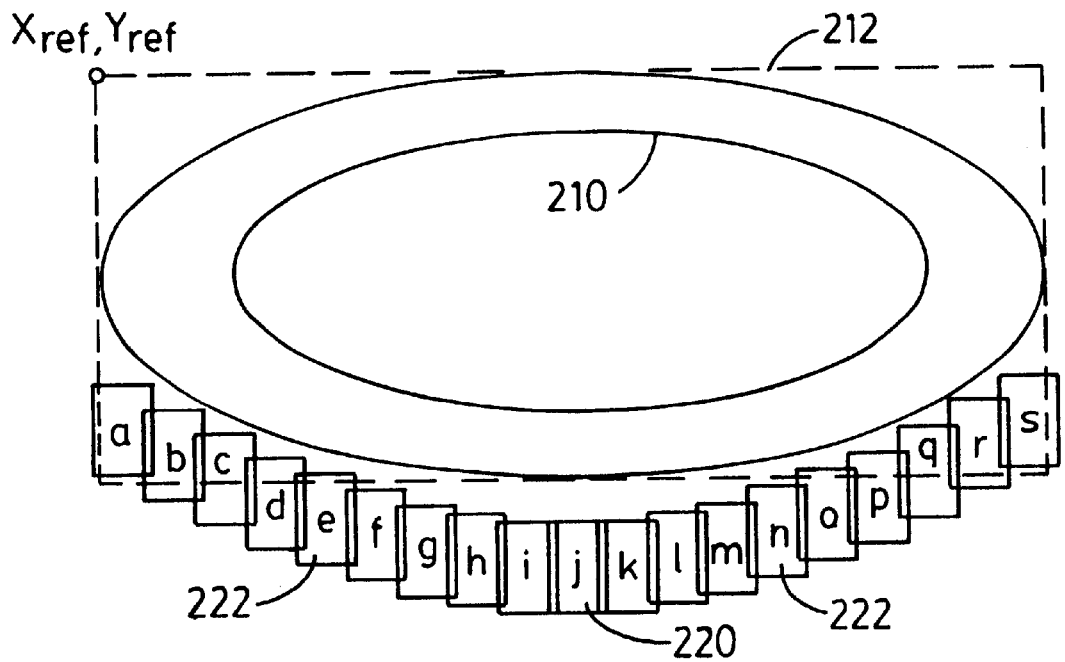
FIG. 8 is an illustration of a binarized video image and showing an alterative embodiment of specific regions of interest within the video image.
Figure 9:
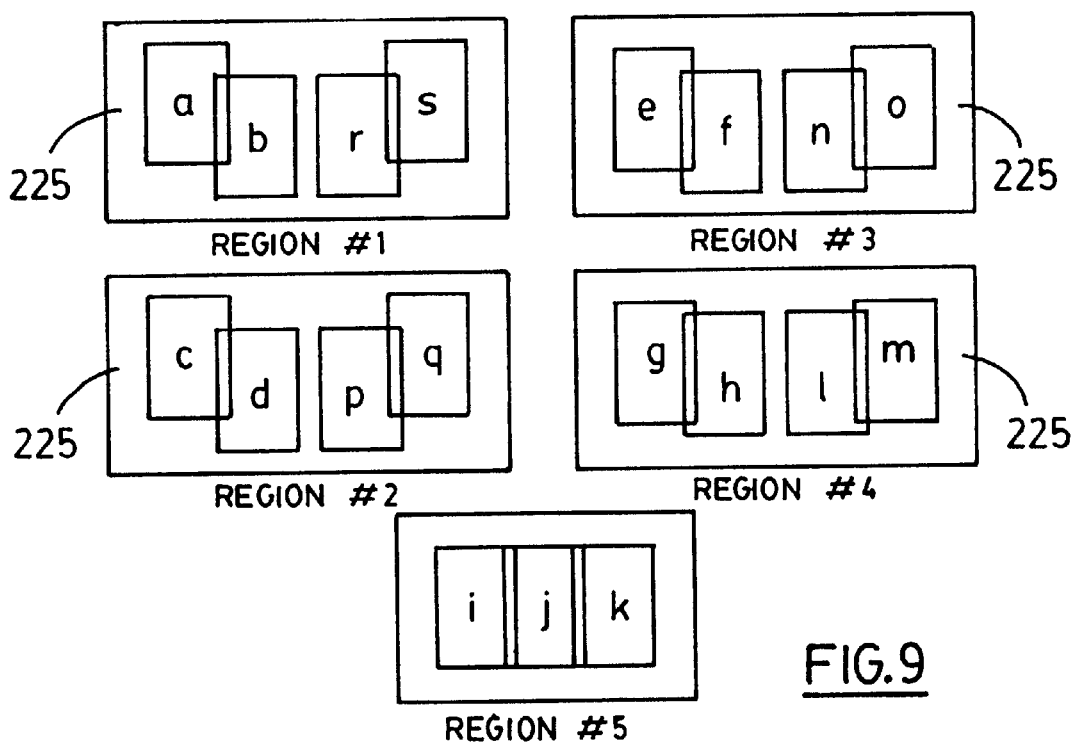
FIG. 9 is an illustration of grouped specific regions of interest shown in FIG. 8.
Figure 10:
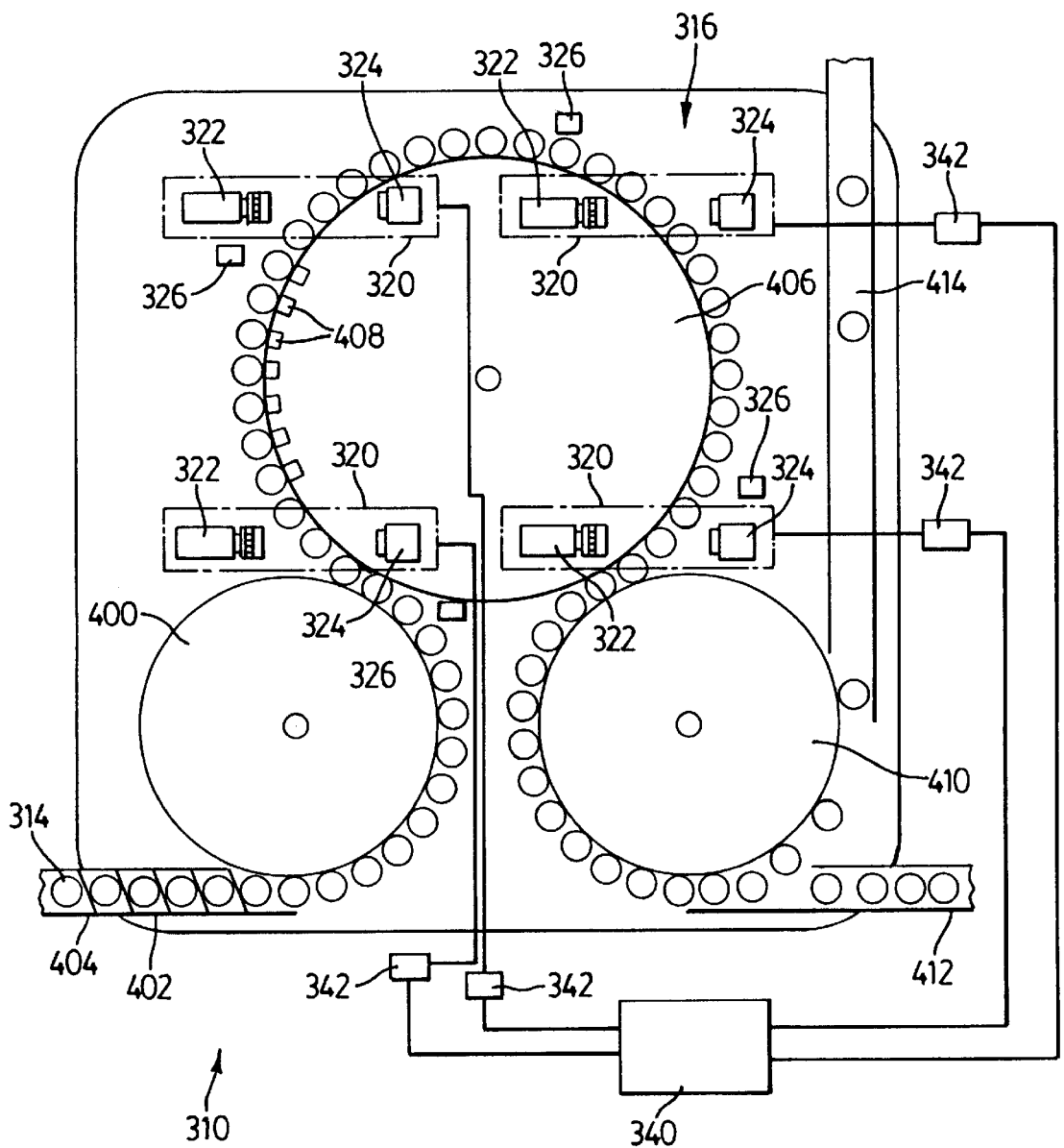
FIG. 10 is a plan view of an alterative embodiment of a bottle production line including an inspection system for detecting bottle defects.
Figure 11:
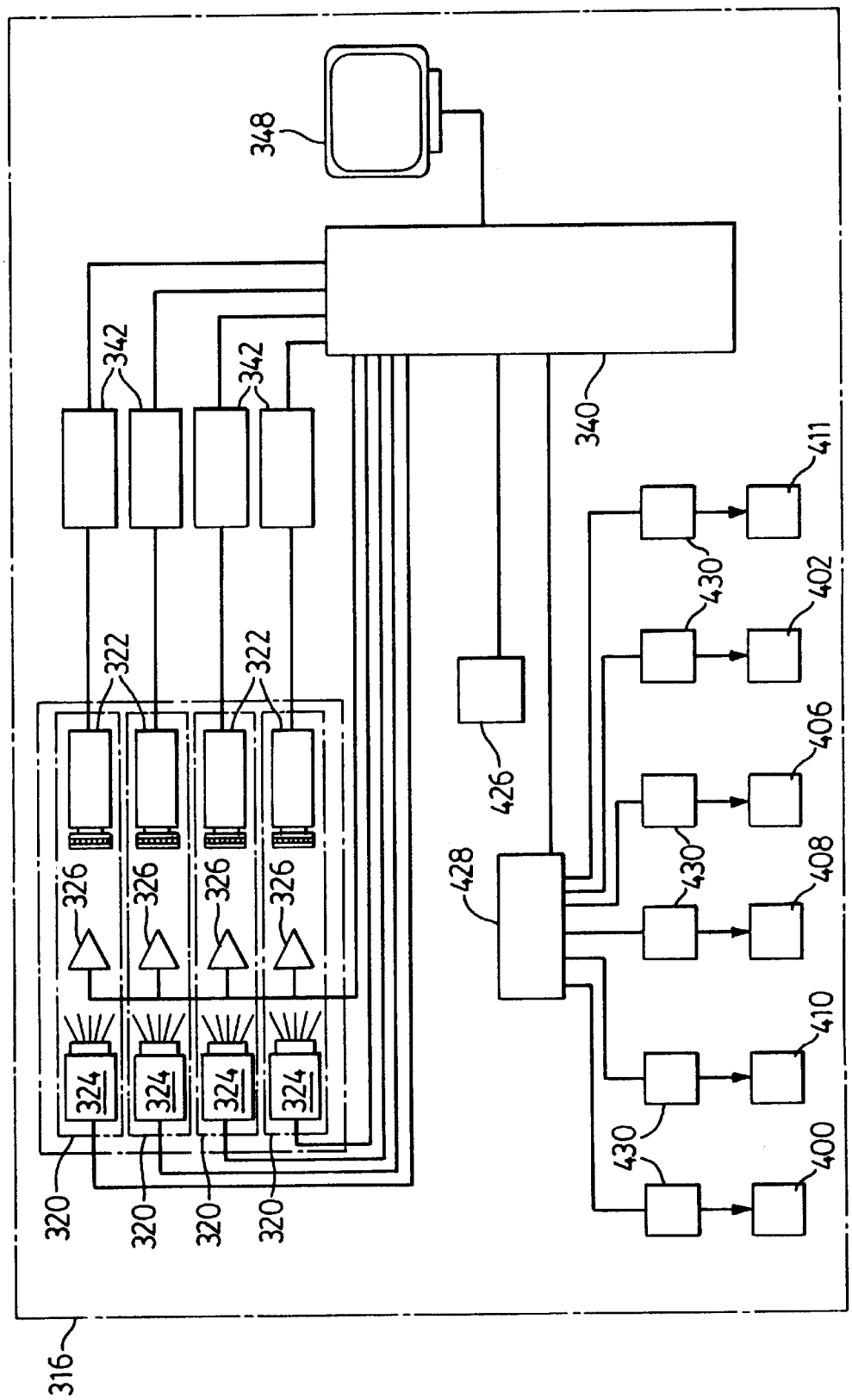
FIG. 11 is a schematic block diagram of the inspection system illustrated in FIG. 10.

Although FIG. 6 illustrates 21 side-by-side specific regions of interest, each of which is processed individually to detect thread defects, those of skill in the art will appreciate that the number and orientation of the specific regions of interest within the video image can be varied. For example, FIGS. 8 and 9 show an alternative arrangement of specific regions of interest within the video image. In this embodiment, the CPU binarizes the pixels within the window to locate the reference feature (i.e. the bottle rim 210) in the same manner previously described. An enclosing rectangle 212 aligned with the scan lines which encompasses the bottle rim 210 is defined and the top-left corner oft he enclosing rectangle is used as the reference location Xref, Yref. A central specific region of interest 220 is then determined. Once the central specific region of interest has been determined, nine other rectangular specific regions of interest 222 on both sides of the central specific regions of interest are determined giving a total of nineteen specific regions of interest. The specific regions of interest slightly overlap with adjacent specific regions of interest and as in previous embodiment, are increasingly offset in the Y-direction direction the further they are from the central specific region of interest to follow the threads of a bottle in the video image.

Once the specific regions of interest 220, 222 have been determined, the CPU calculates a threshold value for each of the specific regions of interest. With the threshold values established for the specific regions of interest, the CPU compares the pixels in the specific regions of interest with the threshold values to create binarized pixels in a similar manner to that previously described. Following this and unlike the previous embodiment, the CPU groups the nineteen specific regions of interest into five groups 225 depending on the relative positions of the specific regions of interest with respect to the central region of interest. Blob detection is then performed on the groups 225 of binarized pixels to locate contiguous white pixels in each group 225. The CPU then collects a histogram for each group 225 by counting the number of contiguous white pixels. The histograms collected for the groups 225 are then scaled according to their positions relative to the central specific region of interest to correct for perspective effects. Once scaled, the number of contiguous white pixels in the groups are compared with a threshold area value. If the numbers of contiguous white pixels are greater than the threshold area value, the contiguous white pixels are filtered in the manner described previously before the contiguous white pixels are determined to represent thread defects.

Referring now to FIGS. 10 to 13, an alternative embodiment of a bottle production line 310 including an inspection system 316 for detecting bottle defects is shown. As can be seen, the inspection system 316 includes a starwheel 400 which receives a stream of separated bottles 314 from a feedscrew 402 at the output end of an inlet conveyor 404. The stark 400 delivers the bottles to the pockets of a main starwheel 406 which incorporates backrest gripers 408 to secure the bottles to the main starwheel and prevent the bottles from rotating or vibrating The main starwheel 406 in turn delivers the bottles to the pockets of another starwheel 410 which delivers the bottles either to an outlet conveyor 412 or to a bottle rejection conveyor 414. Video imaging sections 320 are disposed about the periphery of the main starwheel 408 at circmferentially spaced locations to in a different portion of each bottle as it is moved by the main starwheel.

Each video image section includes a photoelectric bottle detection sensor 326 which detects the arrival of a bottle. The bottle detection sensor 326 when triggered signals a computer 340 which in turn triggers a strobe light 324. A CCD camera 322 is associated with each strobe light to take an image of the backlit bottle when the strobe light is triggered. Video image processors 342 capture and process the video images taken by the CCD cameras 332 when the strobe lights are operated.

The computer 340 is connected to an operator monitor 348 and to a central control system 426 so that the operation of the inspection system can be coordinated with the operation of the remainder of the bottle fly. The computer 340 also communicates with a programmable logic controller (PLC) 428. PLC 428 communicates with drive controllers 430 associated with the starwheels 400, 406 and 410, backrest grippers 408, inlet feedscrew 402 and starwheel clamps 411.

Referring now to FIG. 12, the orientation of the CCD camera 322 and strobe light 324 in one oft he video imaging sections is better illumed. As can be seen, the CCD camera 322 is oriented so that its optical axis points downwardly towards the bole at an angle equal to about 45° with respect to the horizontal H. The strobe light 324 is similarly oriented so that it directs light towards the bottle at an inclined angle with respect to the horizontal H equal to about 30°.

The captured video images are processed by the video image processors 342 in a similar manner to that previously described to detect bottle thread defects as illustrated FIG. 13. As can be seen, in this embodiment the CPU determines five side-by-side specific regions of interest 440 following the bottle threads in the video image. In this embodiment, when a defective bottle is detected by the CPU within the computer 340, the computer 340 controls the starwheel 410 so that a bottle is delivered to the defective bottle conveyor 414 rather than the outlet conveyor 412. In this manner, defective bottles are removed from the bottle production line 310.

Although the inspection systems have been described as including four video imaging sections, those of skill in the art will appreciate that additional or fewer video imaging sections can be used depending on the desired accuracy. Also, although each video imaging processor has been described as having a dedicated CPU to process the captured video images, it should be realized that the number of motherboard may be decreased with each motherboard processing video images captured by more than one daughterboard. Also, although a bottle detection sensor is shown for each video imaging section, it should be realized that a single bottle detection sensor can be used to detect each bottle as it approaches the inspection system. In this case, the output of the encoder is used to determine the speed of the bottles and the triggering of the CCD cameras is based on the determined bottle speed and the spacing between successive video imaging sections.

Although specific embodiments of the present invention have been described, those of skill in the an will appreciate that variations and/ or modifications may be made without departing from the scope thereof as defined by the appended claims.

I claim:

1. A method of inspecting bottles having a threaded section for thread defects as said bottles move along a high speed production line without requiring handling or manipulation of said bottles during thread defect inspection, said method comprising the steps of:

capturing video images of each bottle with video cameras as each said bottle moves into the fields of view of said video cameras irrespective of the position of each said bottle within said fields of view, each video image encompassing a general region of interest containing a different portion of the threaded section of each said bottle;

for each video image, processing pixels of said video image to highlight pixels corresponding to defects in said threaded section and corresponding to a reference feature of said bottle;

determining for each video image, the location of said reference feature based on highlighted pixels;

determining for each video image, the position of said threaded section of said bottle within said general region of interest based on the location of said reference feature;

for each video image, segmenting a portion of said general region of interest, which encompasses said portion of said threaded section into at least one specific region of interest; and for each video image, examining the pixels of the video image in said at least one specific region of interest to detect thread defects generally about the circumference of said bottle.

2. The method of claim 1 wherein said feature is the top rim of said bottle.

3. The method of claim 2 wherein highlighted pixels corresponding to said top rim define a torus and wherein the portion of said general region of interest and the position of said at least one specific region of interest are determined based on the position of said torus.

4. The method of claim 3 wherein said general region of interest is segmented into a plurality of specific regions of interest including a central specific region of interest the position of the central specific region of interest being determined relative to said torus and wherein the positions of other specific regions of interest on opposite sides of said central specific region of interest are determined relative to the position of said central specific region of interest.

5. The method of claim 4 wherein said other specific regions of interest are increasingly offset in a Y-direction the further they are from said central specific region of interest to follow the threaded section of said bottle in said video image.

6. The method of claim 5 wherein said specific regions of interest decrease in an X-direction the further they are from said central specific region of interest to compensate for perspective effects.

7. The method of claim 6 wherein said specific regions of interest are positioned side-by-side.

8. The method of claim 6 wherein said specific regions of interest overlap adjacent specific regions of interest.

9. The method of claim 3 wherein said step of examining said pixels includes the steps of:

determining a black/white pixel threshold value for said specific regions of interest;

comparing said pixels with said threshold value and binarizng said pixels as white or black depending on the results of said comparison; and determining groups of contiguous white pixels larger than a threshold value thereby to detect thread defects.

10. The method of claim 9 wherein during the step of determining groups of contiguous white pixels, the groups of contiguous white pixels are filtered to reduce false detection of bottle thread defects.

11. The method of claim 1 wherein steps (i) to (iv) are performed at a plurality of circumferentially spaced locations about said bottle to detect thread defects in the entire threaded section of said bottle.

12. The method of claim 1 wherein during pixel processing of each said video image, said highlighted pixels are white and remaining pixels are black.

13. The method of claim 12 wherein said reference feature is the top rim of said bottle and wherein said corresponding highlighted pixels take the form of a torus.

14. The method of claim 13 wherein said examining step includes the step of determining groups of contiguous white pixels larger than a threshold value thereby to detect thread defects.

15. The method of claim 13 wherein blob detection is performed on pixels of each said video image to locate the highlighted pixels resembling said torus.

16. The method of claim 14 wherein blob detection is used to determine said groups of contiguous white pixels.

17. A system for inspecting bottles having a threaded section for thread defects as said bottles are moved along a production line without requiring handling or manipulation of said bottles during thread defect inspection, said system comprising:

a plurality of video imaging sections disposed along said production line at spaced locations, each video imaging section being oriented with respect to said production line to take a video image of each bottle at a different circumferential region thereof as each bottle moves into the field of view of said video imaging section irrespective of the position of each said bottle within said field of view, each video image encompassing a general region of interest containing a different portion of the threaded section of each bottle; and processing means in communication with said video imaging section and receiving the video images taken thereby, said processing means processing in real-time each video image to:

highlight pixels of each video image corresponding to defects in said threaded section and corresponding to a reference feature of said bottle;

determine the location of said reference feature based on highlighted pixels;

determine the position of the threaded section of said bottle within said general region of interest based on the location of said reference feature;

segment a portion of said general region of interest, which encompasses said portion of said threaded section into at least one specific region of interest; and examine the pixels in said at least one specific region of interest to detect thread defects generally about the circumference of said bottle.

18. A system for inspecting bottles as defined in claim 17 wherein each video imaging section includes a video imaging camera and a light source, said light source and said video imaging camera being located on opposite sides of said production line, the video imaging cameras and light sources in said video imaging sections being oriented so that video images of the entire circumference of each bottle are taken by said video imaging sections.

19. A system for inspecting bottles as defined in claim 18 further comprising at least one bottle detection sensor for detecting the presence of a bottle, said processing means being responsive to said at least one bottle detection sensor and triggering said video imaging sections to take video images of said bottle.

20. A system for inspecting bottles as defined in claim 19 wherein said light sources remain illuminated and wherein said processing means triggers the video imaging camera to take an image of said bottle in response to the associated bottle detection sensor.

21. A system for inspecting bottles as defined in claim 20 wherein said processing means signals a bottle reject mechanism along said production line upon detection of a bottle having a thread defect.

22. A system for inspecting bottles as defined in claim 18 wherein said video imaging sections are arranged in interlocking pairs to reduce spacing and optical interference therebetween.

23. A system for inspecting bottles each having a threaded section for thread defects as said bottles are moved along a high speed production line without requiring handling or manipulation of said bottles during thread defect inspection, said system comprising:

a plurality of video imaging sections disposed along said production line at spaced locations, each video imaging section being positioned with respect to said production line to take a video image of each bottle neck at a different circumferential region thereof as each bottle moves into the field of view of said video imaging section irrespective of the position of said bottle within said field of view, said video imaging sections being arranged in pairs oriented to reduce spacing and optical interference therebetween; and processing means in communication with said video imaging sections and receiving the video images taken thereby, said processing means processing each said video image to:

highlight pixels corresponding to defects in said threaded section and corresponding to the top rim of said bottle;

determine for each video image the location of said top rim based on highlighted pixels;

determine the position of threads of said bottle neck within said general region of interest based on the location of said top rim;

segment at least a portion of each video image, which encompasses said threads into a plurality of specific regions of interest based on the location of said top rim; and process each specific region of interest independently to determine defects in each of said specific regions of interest based on the existence of areas of white pixels larger than a prescribed threshold area size within said specific regions of interest.

24. A system for inspecting bottles as defined in claim 23 wherein each video imaging section includes a video imaging camera and a fight source, the video imaging camera and light source being positioned on opposite sides of said production line and being laterally offset so that the optical axis of each video imaging section forms an oblique angle with respect to said production line.

25. A system for inspecting bottles as defined in claim 24 wherein said system includes four video imaging sections arranged in an upstream pair and a downstream pair, the video imaging cameras and light sources in said upstream pair forming an obtuse angle with respect to said production line and the video imaging cameras and light sources in said downstream pair forming acute angles with respect to said production line.

26. A system for inspecting bottles defined in claim 25 wherein the positions of said video imaging cameras and light sources with respect to said production line alternate in successive video imaging sections.

27. A method for detecting thread defects in a bottle having threads about a neck of said bottle comprising the steps of:

capturing video images of said bottle about the circumference of said neck to image said neck;

processing pixels of each video image to highlight pixels corresponding to defects in said threads and corresponding to the top rim of said bottle;

determining for each video image the location of said top rim based on highlighted pixels;

determining the position of the threads of said bottle within said general region of interest based on the location of said top rim;

segmenting at least a portion of each video image, which encompasses said threads into a plurality of specific regions of interest based on the location of said top rim; and video processing each specific region of interest independently to determine defects in each of said specific regions of interest based on the existence of areas of white pixels larger than a prescribed threshold area size within said specific regions of interest.

28. A system for detecting thread defects in a bottle having threads about a neck of said bottle, comprising:

means for capturing video images of said bottle about the circumference of said neck;

means for processing pixels of each video image to highlight pixels corresponding to defects in said threads and corresponding to the top rim of said bottle;

means for determining for each video image the location of said top rim based on highlighted pixels;

means for determining the position of the threads of said bottle neck within said general region of interest based on the location of said top rim;

means for segmenting at least a portion of each video image into a plurality of specific regions of interest based on the location of said top rim; and means for video processing each specific region of interest independently to determine defects in each of said specific regions of interested based on the existence of white areas of white pixels larger than a prescribed threshold area size within said specific region of interest.

29. A method of inspecting bottles having a threaded section for thread defects as said bottles move along a high speed production line without requiring handling or manipulation of said bottles during thread defect inspection, said method comprising the steps of:

capturing video images of each bottle with video cameras as each said bottle moves into the fields of view of said video cameras irrespective of the position of each said bottle within said fields of view, each video image encompassing a general region of interest containing a different portion of the threaded section of said bottle;

determining for each video image, the location of a rim of said bottle within said video image;

determining for each video image the position of said threaded section of said bottle within said general region of interest based on the location of the rim of said bottle;

for each video image segmenting a portion of said general region of interest, which encompasses said portion of said threaded section into a plurality of specific regions of interest, said specific regions of interest including a central specific region of interest and other specific regions on opposite sides of said central specific region of interest, the position of said central specific region of interest being determined based on the location of said rim; and for each video image examining pixels of the video image in said specific regions of interest to detect thread defects generally about the circumference of said bottle.

30. The method of claim 29 wherein said other specific regions of interest are increasingly offset in a Y-direction the further they are from said central specific region of interest to follow the threaded section of said bottle in said video image.

31. The method of claim 30 wherein said specific regions of interest decrease in a X-direction the further they are from said central specific region of interest to compensate for perspective effects.

32. The method of claim 31 wherein said specific regions of interest are positioned side-by-side.

33. The method of claim 31 wherein said specific regions of interest overlap adjacent specific regions of interest.

* * * * *